United States Patent
Han (10) Patent No.: US 10,529,442 B2
(45) Date of Patent: Jan. 7, 2020

(54) METHOD FOR MEASURING A CHANGE IN AN INDIVIDUAL'S IMMUNOREPERTOIRE

(71) Applicant: CB BIOTECHNOLOGIES, INC., Huntsville, AL (US)

(72) Inventor: Jian Han, Huntsville, AL (US)

(73) Assignee: iRepertoire, Inc., Huntsville, AL (US)

( * ) Notice: Subject to any disclaimer, the term of this patent is extended or adjusted under 35 U.S.C. 154(b) by 534 days.

(21) Appl. No.: 15/060,992

(22) Filed: Mar. 4, 2016

(65) Prior Publication Data

US 2016/0259884 A1  Sep. 8, 2016

Related U.S. Application Data

(60) Provisional application No. 62/129,706, filed on Mar. 6, 2015.

(51) Int. Cl.
G06F 19/20 (2011.01)
G16B 25/00 (2019.01)

(52) U.S. Cl.
CPC .................................. G16B 25/00 (2019.02)

(58) Field of Classification Search
CPC . C12Q 1/6869; C12Q 2549/119; G16H 50/20
See application file for complete search history.

(56) References Cited

U.S. PATENT DOCUMENTS

| 9,234,240 B2 * | 1/2016 | Quake | C12Q 1/6883 |
| 2010/0021896 A1 * | 1/2010 | Han | C12Q 1/686 |
| | | | 435/6.16 |
| 2012/0171725 A1 * | 7/2012 | Han | C12P 19/34 |
| | | | 435/91.2 |
| 2014/0065629 A1 | 3/2014 | Barken | |
| 2014/0235478 A1 | 8/2014 | Quake et al. | |

FOREIGN PATENT DOCUMENTS

| WO | 2013036459 A3 | 3/2013 |
| WO | 2014008448 A1 | 1/2014 |
| WO | 2014124451 A1 | 8/2014 |
| WO | 2014189635 A1 | 11/2014 |
| WO | 2016086029 A1 | 6/2016 |

OTHER PUBLICATIONS

Six, A et al. The pest, present, and future of Immune repertoire biology—the rise of next-generation repertoire analysis. Front Immunol. Nov. 27, 2013; vol. 4, No. 413.
Wang C et al: "High throughput sequencing reveals a complex pattern of dynamic interrelationships among human T cell subsets", Proceedings of the National Academy of Sciences, vol. 107, No. 4, Jan. 4, 2010 (Jan. 4, 2010), pp. 1518-15.

* cited by examiner

*Primary Examiner* — David C Thomas
(74) *Attorney, Agent, or Firm* — Maynard Cooper & Gale, P.C.; Matthew J. Parker (57) ABSTRACT

The present invention pertains to methods for determining the change in the immune repertoire of an individual suffering from disease or undergoing therapy for the treatment of a disease. The methods use the difference between the change in the level of immune cell diversity seen in an individual before, during or after a health event to determine the effect of the disease, or the effect of a treatment regime, on the individual. The difference in the level of immune cell diversity is referred to as the Delta Index and is defined as the quantitative and qualitative change (gain or loss of clones) of an individual's most dynamic immune cells over time.

17 Claims, 5 Drawing Sheets

FIG. 1

Sample: PAT1S1 ; Total reads: 3974309 ; Unique CDR3s: 449654 ; top 1000 CDR3s: 20.43%
Sample: PAT1S1 ; Total reads: 3974309 ; Unique CDR3s: 449654 ; top 1000 CDR3s: 20.43%
Sample: PAT1S2 ; Total reads: 4052780 ; Unique CDR3s: 455230 ; top 1000 CDR3s: 19.97%
Sample: PAT1S3 ; Total reads: 4303142 ; Unique CDR3s: 461171 ; top 1000 CDR3s: 20.10%
Sample: PAT2S1 ; Total reads: 5118708 ; Unique CDR3s: 342145 ; top 1000 CDR3s: 21.60%
Sample: PAT2S2 ; Total reads: 5533076 ; Unique CDR3s: 346387 ; top 1000 CDR3s: 21.24%
Sample: PAT2S3 ; Total reads: 5801681 ; Unique CDR3s: 344977 ; top 1000 CDR3s: 21.59%
Sample: PAT3S1 ; Total reads: 901356 ; Unique CDR3s: 221187 ; top 1000 CDR3s: 32.59%
Sample: PAT3S2 ; Total reads: 922392 ; Unique CDR3s: 220299 ; top 1000 CDR3s: 32.55%
Sample: PAT3S3 ; Total reads: 3758122 ; Unique CDR3s: 84737 ; top 1000 CDR3s: 37.02%
Sample: PBT1S1 ; Total reads: 3758122 ; Unique CDR3s: 84737 ; top 1000 CDR3s: 37.02%

FIG. 2

PAT1S1 data process steps

| A<br>Raw data | | B<br>Normalized to 10M | | C<br>Obtain a fraction | |
|---|---|---|---|---|---|
| ASSEDRDQETGY | 34476 | ASSEDRDQETGY | 86747.155292 | ASSEDRDQETGY | 0.008675 |
| ASSLPQGGSGKLF | 24216 | ASSLPQGGSGKLF | 60931.346808 | ASSLPQGGSGKLF | 0.006093 |
| ASSEAGSTNDPQH | 22638 | ASSEAGSTNDPQH | 56960.845269 | ASSEAGSTNDPQH | 0.005696 |
| ASTSPSMGRGVEETGY | 20660 | ASTSPSMGRGVEETGY | 51983.879462 | ASTSPSMGRGVEETGY | 0.005198 |
| ATSGRTSDSINEQF | 17759 | ATSGRTSDSINEQF | 44684.497335 | ATSGRTSDSINEQF | 0.004468 |
| ASSSTGTARLNTEAF | 14006 | ASSSTGTARLNTEAF | 35241.346357 | ASSSTGTARLNTEAF | 0.003524 |
| SARDGSGADTGY | 12756 | SARDGSGADTGY | 32096.145519 | SARDGSGADTGY | 0.003210 |
| ASSPSGCASTGY | 7301 | ASSPSGCASTGY | 18370.489059 | ASSPSGGASTGY | 0.001837 |
| ASSQQVSNYGT | 6812 | ASSQQVSNYGT | 17140.086491 | ASSQQVSNYGT | 0.001714 |
| ASSPAVDSGANVLT | 6228 | ASSPAVDSGANVLT | 15645.487052 | ASSPAVDSGANVLT | 0.001565 |
| SASANPGQCAGNTEAF | 6048 | SASANPGQCAGNTEAF | 15227.739738 | SASANPGQCAGNTEAF | 0.001522 |
| ASSDRFRCGSNEQF | 5948 | ASSDRFRCGSNEQF | 14966.123671 | ASSDRFRCGSNEQF | 0.001497 |
| ASSLSGCFPVETGY | 5482 | ASSLSGCFPVETGY | 13793.592798 | ASSLSGGFPVETQI | 0.001379 |
| ASSDLAIETGY | 5261 | ASSDLAIETGY | 13237.521290 | ASSDLAIETGY | 0.001324 |
| SARDRGTEAF | 4904 | SARDRGTEAF | 12339.251930 | SARDRGTEAF | 0.001234 |
| ASSLGQGTEKLF | 4669 | ASSLGQGTEKLF | 11747.994173 | ASSLGQGTEKLF | 0.001175 |
| ASSFTGGYYNEQF | 4637 | ASSFTGGYYNEQF | 11667.437031 | ASSFTGGVYNEQF | 0.001167 |
| ASSYGLGANVLT | 4025 | ASSYGLGANVLT | 10227.546701 | ASSYGLGANVLT | 0.001013 |
| SASGGRNTEAY | 3963 | SASGGRNTEAY | 9971.544739 | SASGGENTTGY | 0.000997 |
| ASSPGFEAF | 3817 | ASSPGFEAF | 9604.185281 | ASSPGFEAF | 0.000960 |
| ASSIWSTDGY | 3430 | ASSIWSTDGY | 8630.431101 | ASSIWSTDGY | 0.000863 |
| ASKMTGKKGY | 3417 | ASKMTGKKGY | 8597.721013 | ASKWTGEEGY | 0.000860 |
| ASSLGGREGY | 3406 | ASSLGGREGY | 8570.043245 | ASSLGGREGY | 0.000857 |
| ASSRGSENTGELF | 3346 | ASSRGSENTGELF | 8419.073605 | ASSRGSDNTELF | 0.000842 |
| ASSDSPANTEAF | 3345 | ASSDSPANTEAF | 8416.551444 | ASSGSPNTEAP | 0.000842 |
| ASSSGPNTEAF | 3255 | ASSSGPNTEAF | 8190.102984 | ASSSGFNTEAF | 0.000819 |
| ASSLAGGLANESDF | 3228 | ASSLAGGLANESDF | 8122.166646 | ASSLAGGLANESDF | 0.000812 |
| ASRSRLETGY | 3199 | ASRSRLETGY | 8049.197984 | ASRSRLETGY | 0.000805 |
| SARGGTEAF | 3143 | SARGGTEAF | 7908.292989 | SARGGTEAF | 0.000791 |
| ASSEAPFNKVSSNRQPQH | 3140 | ASSEAPFNKVSSNRQPQH | 7900.744507 | ASSEAPFNKVSSNRQPQH | 0.000790 |
| ... | | ... | | | |
| AAGGGFDYGT | 2 | AAGGGFDYGT | 5.032321 | AAGGGFDYGT | 0.000001 |
| AAGGAGSTGELF | 2 | AAGGAGSTGELF | 5.032321 | AAGGAGSTGELF | 0.000001 |
| AAGEWGRNTEAF | 2 | AAGEWGRNTEAF | 5.032321 | AAGEWGRNTEAF | 0.000001 |
| AAGEHSTDGY | 2 | AAGEHSTDGY | 5.032321 | AAGEHSTDGY | 0.000001 |
| AAGETGY | 2 | AAGETGY | 5.032321 | AAGETGY | 0.000001 |
| AAGETGGRGPQH | 2 | AAGETGGRGPQH | 5.032321 | AAGETGGRGPQH | 0.000001 |
| AAGRAF | 2 | AAGRAF | 5.032321 | AAGRAF | 0.000001 |
| AAGSKFSTDGY | 2 | AAGSKFSTDGY | 5.032321 | AAGSKFSTDGY | 0.000001 |
| AAGACTGTGY | 2 | AAGACTGTGY | 5.032321 | AAGACTGY | 0.000001 |
| AAFVGLSSGNTIY | 2 | AAFVGLSSGNTIY | 5.032321 | AAFVGLSSGNTIY | 0.000001 |
| AAFPAGRNTIY | 2 | AAFPAGRNTIY | 5.032321 | AAFPAGRNTIY | 0.000001 |
| AAEIRSSAIREQF | 2 | AAEIRSSAIREQF | 5.032321 | AAEIRSSAIREQF | 0.000001 |
| AAEGSETGY | 2 | AAEGSETGY | 5.032321 | AAEGSETGY | 0.000001 |
| AADGRYTGT | 2 | AADGRYTGT | 5.032321 | AADGRYTGT | 0.000001 |
| AAEERGSSRQPQH | 2 | AAEERGSSRQPQH | 5.032321 | AAEERGSROPQH | 0.000001 |
| AADSWTEAF | 2 | AADSWTEAF | 5.032321 | AADSVTEAF | 0.000001 |
| AADRWNQPQH | 2 | AADRWNQPQH | 5.032321 | AADRWNQPQH | 0.000001 |
| AACEGTEAF | 2 | AACEGTEAF | 5.032321 | AACKGTTEAF | 0.000001 |
| AAATROQPQH | 2 | AAATROQPQH | 5.032321 | AAATROQPQH | 0.000001 |
| AAASTNKVRNTEAF | 2 | AAASTNKVRNTEAF | 5.032321 | AAASTNKVRNTEAF | 0.000001 |
| AAASLAGELF | 2 | AAASLAGELF | 5.032321 | AAASLAGELF | 0.000001 |
| AAARGSTDGY | 2 | AAARGSTDGY | 5.032321 | AAARGSTDGY | 0.000001 |
| AARGEGTEAF | 2 | AARGEGTEAF | 5.032321 | AAARGRGTEAF | 0.000001 |
| AARGANTGT | 2 | AARGANTGT | 5.032321 | AANGANYGT | 0.000001 |
| AAPAGTEAF | 2 | AAPAGTEAF | 5.032321 | AAPAGTEAF | 0.000001 |
| AAALIAAGSPLH | 2 | AAALIAAGSPLH | 5.032321 | AAALIADSPLH | 0.000001 |
| AAAKDRGRNTEAF | 2 | AAAKDRGRNTEAF | 5.032321 | AAAKDRGRNTEAF | 0.000001 |
| AAAIGGPREKGY | 2 | AAAIGGPREKGY | 5.032321 | AAAIGGFRETGY | 0.000001 |
| AAACENTEAF | 2 | AAACENTEAF | 5.032321 | AAAGRNTEAF | 0.000001 |
| AAACSTNQPQH | 2 | AAACSTNQPQH | 5.032321 | AAAGSTNQPQH | 0.000001 |

[449654 rows x 1 columns]    multiply each CDR3s reads by 2.516 (=10,000,000.00/3,974,309)    [449654 rows x 1 columns]    normalized reads count divided by 10 million (total reads).

FIG. 3

PAT1S1 data process steps

Figure showing three data tables (D, E, F) illustrating the PAT1S1 data processing steps:

D — Obtain the difference: Table with columns PAT1S1, PAT1S2, Delta, showing CDR3 sequences and their frequency values. Caption: "Process data from sample PAT1S2 the same way as PAT1S1, and obtain the difference between the two frequencies. Take the absolute values, as some delta maybe positive, and some negative."

E — Sort based on Delta: Table with columns PAT1S1, PAT1S2, Delta, showing CDR3 sequences sorted by Delta value. Caption: "Then, sort the CDR3s based on the ranking of Delta value. Those CDR3s with the most dramatic change will be ranked on top. They are the most dynamic clones."

F — Selecting top x CDR3s: Table with columns PAT1S1, PAT1S2, Delta, showing the top CDR3 sequences. Caption: "Selecting top X number of CDR3s to calculate Delta index. The number x can be 100, 1000, or 10,000, for example. The purpose is to evaluate repertoire changes caused by the group of most dynamic clones."

FIG. 4

Signal optimization

|  | H<br>Top 100 CDR3s | I<br>Top 1000 CDR3s | J<br>Top 10000 CDR3s |
|---|---|---|---|
|  | PAT1S1: 7.45%<br>PAT1S2: 7.09%<br>Average: 7.27%<br>DeltaIndex: 6.53% | PAT1S1: 15.76%<br>PAT1S2: 15.22%<br>Average: 15.49%<br>DeltaIndex: 9.60% | PAT1S1: 27.77%<br>PAT1S2: 27.21%<br>Average: 27.47%<br>DeltaIndex: 18.65% |
|  | PAT1S1: 9.00%<br>PAT2S1: 9.89%<br>Average: 9.45%<br>DeltaIndex: 30.71% | PAT1S1: 17.72%<br>PAT2S1: 19.04%<br>Average: 18.38%<br>DeltaIndex: 30.39% | PAT1S1: 29.48%<br>PAT2S1: 33.52%<br>Average: 31.50%<br>DeltaIndex: 36.12% |
|  | Signal:Noise<br>30.71/6.53=4.7 | Signal:Noise<br>30.39/9.60=3.15 | Signal:Noise<br>36.12/18.65=1.94 |

Figure 4:
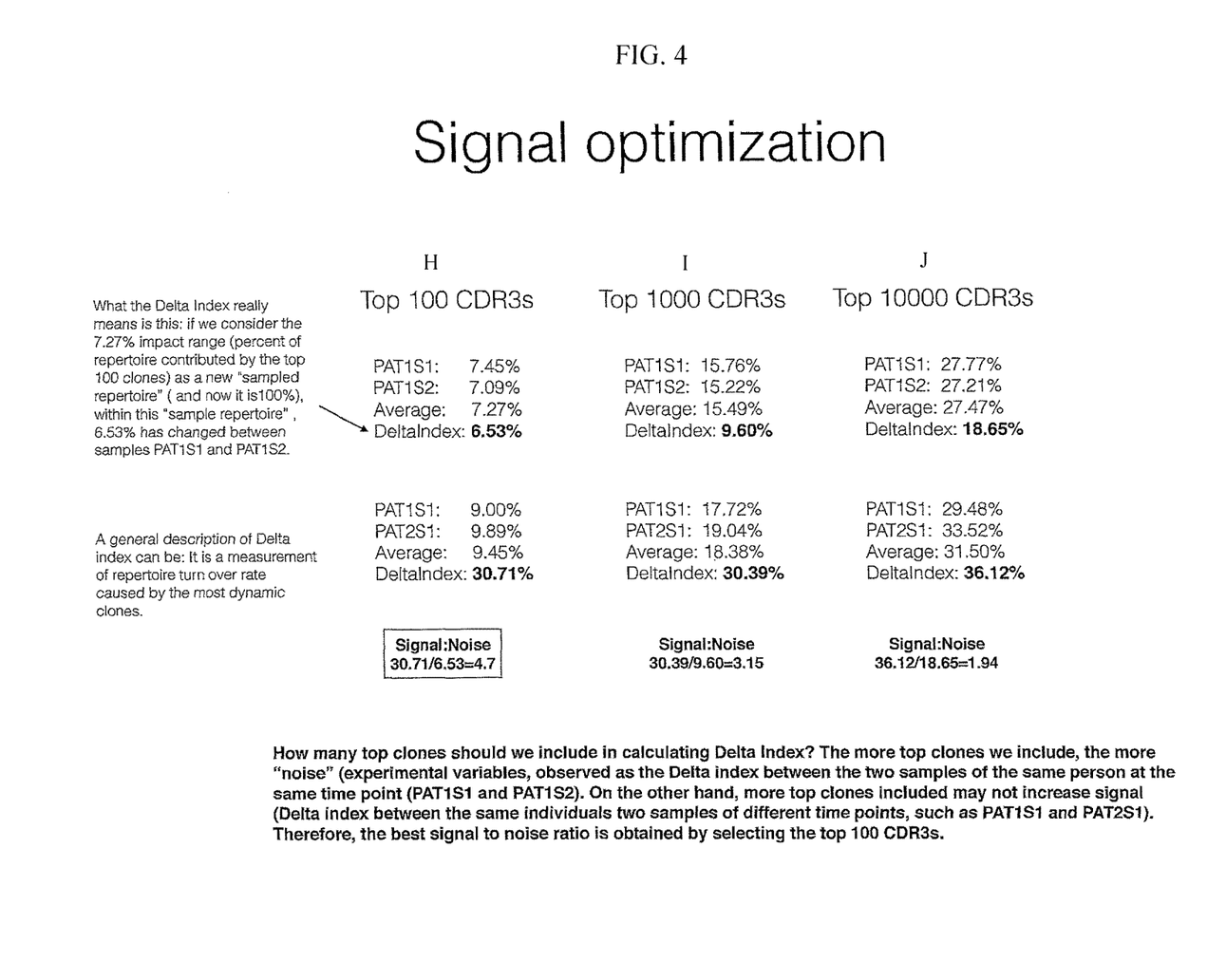
FIG. 4 represents signal optimization for the samples: Column H represents calculation of the signal to noise ratio for an impact range of 100; Column I represents calculation of the signal to noise ratio for an impact range of 1,000; and Column J represents the calculation of the signal to noise ratio for an impact range of 10,000.

What the Delta Index really means is this: if we consider the 7.27% impact range (percent of repertoire contributed by the top 100 clones) as a new "sampled repertoire" (and now it is100%), within this "sample repertoire", 6.53% has changed between samples PAT1S1 and PAT1S2.

A general description of Delta index can be: It is a measurement of repertoire turn over rate caused by the most dynamic clones.

How many top clones should we include in calculating Delta Index? The more top clones we include, the more "noise" (experimental variables, observed as the Delta index between the two samples of the same person at the same time point (PAT1S1 and PAT1S2). On the other hand, more top clones included may not increase signal (Delta index between the same individuals two samples of different time points, such as PAT1S1 and PAT2S1). Therefore, the best signal to noise ratio is obtained by selecting the top 100 CDR3s.

FIG. 5

Results of Delta Index

A    DI for sample pair PAT1S1 / PAT1S1 = 0.00%   → Same sample

B
- DI for sample pair PAT1S1 / PAT1S2 = 6.53%
- DI for sample pair PAT1S1 / PAT1S3 = 5.39%
- DI for sample pair PAT1S2 / PAT1S3 = 5.14%
- DI for sample pair PAT2S1 / PAT2S2 = 5.74%
- DI for sample pair PAT2S1 / PAT2S3 = 5.63%
- DI for sample pair PAT2S2 / PAT2S3 = 6.52%
- DI for sample pair PAT3S1 / PAT3S2 = 3.88%

→ Same individual, same time point, but different samples

C
- DI for sample pair PAT1S1 / PAT2S1 = 30.71%
- DI for sample pair PAT1S1 / PAT2S2 = 30.57%
- DI for sample pair PAT1S1 / PAT2S3 = 31.86%
- DI for sample pair PAT1S2 / PAT2S1 = 33.93%
- DI for sample pair PAT1S2 / PAT2S2 = 33.32%
- DI for sample pair PAT1S2 / PAT2S3 = 34.10%
- DI for sample pair PAT1S3 / PAT2S1 = 32.37%
- DI for sample pair PAT1S3 / PAT2S2 = 31.67%
- DI for sample pair PAT1S3 / PAT2S3 = 32.39%

→ Same individual, different samples at different time points (days interval)

D
- DI for sample pair PAT1S1 / PAT3S1 = 73.95%
- DI for sample pair PAT1S1 / PAT3S2 = 77.15%
- DI for sample pair PAT1S2 / PAT3S1 = 75.07%
- DI for sample pair PAT1S2 / PAT3S2 = 74.92%
- DI for sample pair PAT1S3 / PAT3S1 = 74.56%
- DI for sample pair PAT1S3 / PAT3S2 = 74.37%
- DI for sample pair PAT2S1 / PAT3S1 = 73.80%
- DI for sample pair PAT2S1 / PAT3S2 = 74.51%
- DI for sample pair PAT2S2 / PAT3S1 = 73.37%
- DI for sample pair PAT2S2 / PAT3S2 = 74.61%
- DI for sample pair PAT2S3 / PAT3S1 = 73.54%
- DI for sample pair PAT2S3 / PAT3S2 = 74.75%

→ Same individual, different time points with 3 months interval.

E
- DI for sample pair PAT1S1 / PBT1S1 = 99.84%
- DI for sample pair PAT1S2 / PBT1S1 = 99.87%
- DI for sample pair PAT1S3 / PBT1S1 = 99.86%
- DI for sample pair PAT2S1 / PBT1S1 = 99.91%
- DI for sample pair PAT2S2 / PBT1S1 = 99.88%
- DI for sample pair PAT2S3 / PBT1S1 = 99.90%
- DI for sample pair PAT3S1 / PBT1S1 = 99.89%
- DI for sample pair PAT3S2 / PBT1S1 = 99.90%

→ Different individuals, different time points.

METHOD FOR MEASURING A CHANGE IN AN INDIVIDUAL'S IMMUNOREPERTOIRE

CROSS REFERENCE TO RELATED APPLICATION

This application claims priority to U.S. Provisional Patent Application No. 62/129,706, entitled "Method for Measuring a Change in an Individual's Immunorepertoire" and filed on Mar. 6, 2015, which is incorporated herein by reference.

FIELD OF THE INVENTION

The present disclosure relates to methods for classifying an individual's T and B lymphocytes at the single cell level, based on the lymphocytes' differentially-expressed receptors and unique CDR3 sequences, and methods to determine a change in an individual's immune repertoire before, during and/or after disease and/or treatment of such disease.

BACKGROUND OF THE INVENTION

Through the process of homeostasis, the immune system maintains a certain number and repertoire of T and B lymphocytes, collectively referred to as an individual's "immune repertoire." An individual's immune repertoire constantly changes, however, as a result of continuous cell turnover and the exposure to antigens. Such immune repertoire changes may include, for example, the generation of new (naive) T and B lymphocytes, expansion of active T and B lymphocytes, and the formation of new memory T and B lymphocytes.

Immune therapies and cellular therapies are becoming increasingly popular tools for the treatment of cancer and autoimmune disease. Immune therapies may include antibody treatments to modulate immune pathways or to boost a patient's immune response to a disease. Cellular therapies may include exposing a patient's blood or white blood cells to a disease antigen ex vivo and subsequently reintroducing the treated blood or white blood cells to the patient. While conventional methods utilize synthetic small molecules to target particular disease pathways, immune therapies and cellular therapies may act by educating a patient's immune system to fight disease.

When in a disease state, or during treatment of such disease state, a patient's immune system mobilizes to fight the disease. As a result, the turnover rate of the immune repertoire may change. A measurement of such change may give an indication of the effectiveness of the treatment. Currently, however, no tools or methods are available which would allow scientists or physicians to measure the immune repertoire turnover rate; current methods, such as white blood cell counts and flow cytometry, are not ideal. Measuring a patient's white blood cell count provides only the total number of lymphocytes or the number of cells that belong to lymphocyte category, and flow cytometry allows classification of T and B lymphocytes based on surface markers. Neither of these methods, however, provides an accurate measurement of the immune repertoire turnover rate. As such, current methods are not ideal for the evaluation of therapeutic results of therapies, such as immune therapies, the generation of markers for pre-screening patients, and the identification of those patients best fit for a particular therapy. What is needed, therefore, is a tool to classify T and B lymphocytes at the single cell level based on the differentially-expressed T or B lymphocyte receptors and a method of utilizing this information to determine a change in an individual's immune repertoire.

SUMMARY OF THE INVENTION

In one embodiment, the present disclosure relates to a method of calculating the change in the immune repertoire of an individual, wherein such change is a measurement of the turnover rate of the most dynamic immune cells. The method may comprise quantifying clonotypes (i.e., clonal types) in populations of immune cells from two or more samples collected from the same patient. In one embodiment, frequency data is calculated for two or more samples by identifying the frequency of each clonotype, wherein the frequency data are normalized to correct for sample differences. The absolute qualitative and quantitative differences in the frequency of each clonotype in the patient samples may then calculated to determine the clonotypes, common to each sample, with the largest frequency change. The method may then comprise determining the percentage of the clonotypes with the highest degree of change between samples. The samples may be collected at the same time point to determine an individual's baseline immune repertoire, or collected at different time points to calculate the immune repertoire change rate. In certain embodiments, the immune repertoire change rate is determined at time point before, during or after a health event. The presently disclosed methods allow for the analysis of a vast amount of sequencing data while eliminating sampling and sequencing inconsistencies that have previously made the calculation of immune repertoire changes impossible.

BRIEF DESCRIPTION OF THE FIGURES

The disclosure can be better understood with reference to the following figures.

FIG. 2 illustrates the calculations utilized in determining normalized sequence data: Column A represents raw sequence data and columns B and C represent normalized data.

FIG. 5 illustrates the calculated Delta Index for several sample groups: Group A represents a single sample taken from one patient, where the sample is split into two subsamples; Group B represents multiple samples taken from the same individual at the same time point; Group C represents samples taken from the same individual at two different time points with an interval of one or two days; Group D represents samples taken from the same individual at two different time points with an interval of three months; and Group E represents samples taken from different individuals at different time points. In this situation the Delta Index is expected to be near 100%.

DETAILED DESCRIPTION

The inventor has developed a method for determining the change in the immune repertoire of an individual suffering from disease or undergoing therapy for the treatment of a disease. The methods use the difference between the change in the level of immune cell diversity seen in an individual before, during or after a health event to determine the effect of the disease, or the effect of a treatment regime, on the individual. Such a health event may include, in one embodiment, a natural occurrence (i.e., the onset of a disease) or an artificial occurrence (i.e., the commencement of disease treatment). In one aspect of the invention, the difference in the level of immune cell diversity is referred to as the Delta Index. The Delta Index is defined herein as the quantitative change (up or down regulation of CDR3s) and qualitative change (gain or loss of clones) of an individual's most dynamic immune cells over time. In one embodiment, the present invention determines the change in the third complementarity-determining region (CDR3), a region whose nucleotide sequence is unique to each T or B cell clone. In one embodiment, the most dynamic immune cells within an individual's immune system are referred to as the immune repertoire impact range. In one embodiment, the impact range is defined as the 100 CDR3 clones within a sample population which display the most change in their nucleotide sequence. In other embodiments, the impact range may include other numbers of clones, for example the 1,000 or 10,000 clones displaying the biggest change. As used herein, "immune cells" refers to T lymphocytes and/or B lymphocytes.

The methods of the invention may be performed using the following steps for assessing the rate of change in an individual's most dynamic immune cells over time: (a) collecting at least two sample populations of white blood cells from a subject; (b) separately amplifying polynucleotides from each population of white blood cells in a reaction mix comprising target-specific nested primers to produce a set of first amplicons, at least a portion of the target-specific nested primers comprising additional nucleotides which, during amplification, serve as a template for incorporating into the first amplicons a binding site for at least one common primer; (c) separately transferring a portion of each of the first reaction mixes containing the first amplicons to second reaction mixes comprising at least one common primer; (d) for each population, amplifying, using the at least one common primer, the first amplicons to produce a set of second amplicons; (e) sequencing each of the second amplicons to identify the frequency of specific CDR3 regions present in the sample; (f) normalizing the CDR3 frequency data; (g) comparing the normalized CDR3 frequency data of the first sample and the second sample to determine the absolute difference between the frequency of each CDR3 sequence; (h) determining the CDR3 sequences common to the first sample and the second sample with the largest frequency changes; and (i) determining the sequences from step (h) with the highest degree of change. As used herein, "subject" means either a human or an animal.

It has previously been difficult to assess the immune system in a broad manner, as the number and variety of cells in a human or animal immune system is so large that sequencing more than a small subset of cells has been impractical. The inventor developed a semi-quantitative PCR method (amplicon rescue multiplex polymerase chain reaction, or "arm-PCR", described in more detail in U.S. Pat. No. 7,999,092 herein incorporated by reference in its entirety), which provides increased sensitivity and specificity over previously-available methods, while producing semi-quantitative results. It is this ability to increase specificity and sensitivity, and thereby increase the number of targets detectable within a single sample, that makes the method ideal for detecting relative numbers of clonotypes of the immune repertoire. The inventor has more recently discovered that using this sequencing method allows him to compare the change, or turnover rate, of the immune repertoire of individual subjects, which has led to the development of the present method. The method has been used to evaluate subjects who are undergoing treatment for a particular disease, for example cancer. The inventor has demonstrated that a change in the immune repertoire diversity can be readily detected using the methods of the invention. These methods may therefore be useful as indicators of treatment effectiveness, much as cell counts and biochemical tests are currently used in clinical practice.

Clonotypes of an immune repertoire are determined by the rearrangement of Variable (V), Diverse (D) and Joining (J) gene segments through somatic recombination in the early stages of immunoglobulin (Ig) and T cell receptor (TCR) production of the immune system. The V(D)J rearrangement can be amplified and detected from T cell receptor alpha, beta, gamma, and delta chains, as well as from immunoglobulin heavy chain (IgH) and light chains (IgK, IgL). Cells may be obtained from a patient by obtaining peripheral blood, lymphoid tissue, cancer tissue, or tissue or fluids from other organs and/or organ systems, for example. Techniques for obtaining these samples, such as blood samples, are known to those of skill in the art. "Quantifying clonotypes," as used herein, means counting, or obtaining a reliable approximation of, the numbers of cells belonging to a particular clonotype. Cell counts may be extrapolated from the number of sequences detected by PCR amplification and sequencing.

The CDR3 region, comprising about 30-90 nucleotides, encompasses the junction of the recombined variable (V), diversity (D) and joining (J) segments of the gene. It encodes the binding specificity of the receptor and is useful as a sequence tag to identify unique V(D)J rearrangements.

Aspects of the invention include arm-PCR amplification of CDR3 regions from T cells, B cells, and/or subsets of T or B cells. The term "population" of cells, as used herein, therefore encompasses what are generally referred to as either "populations" or "sub-populations" of cells. Large numbers of amplified products may then be efficiently sequenced using next-generation sequencing platforms.

The arm-PCR method provides highly sensitive, semi-quantitative amplification of multiple polynucleotides in one reaction. The arm-PCR method may also be performed by automated methods in a closed cassette system (iCubate®, Huntsville, Ala.), which is beneficial in the present method because the repertoires of various T and B cells, for example, are so large. In the arm-PCR method, target numbers are increased in a reaction driven by DNA polymerase, which is the result of target-specific primers being introduced into the reaction. An additional result of this amplification reaction is the introduction of binding sites for common primers which will be used in a subsequent amplification by transferring a portion of the first reaction mix containing the first set of amplicons to a second reaction mix comprising common primers. "At least one common primer," as used herein, refers to at least one primer that will bind to such a binding site, and includes pairs of primers, such as forward and reverse primers. This transfer may be performed either by recovering a portion of the reaction mix from the first amplification reaction and introducing that sample into a second reaction tube or chamber, or by removing a portion of the liquid from the completed first amplification, leaving behind a portion, and adding fresh reagents into the tube in which the first amplification was performed. In either case, additional buffers, polymerase, etc., may then be added in conjunction with the common primers to produce amplified products for detection. The amplification of target molecules using common primers gives a semi-quantitative result wherein the quantitative numbers of targets amplified in the first amplification are amplified using common, rather than target-specific primers—making it possible to produce significantly higher numbers of targets for detection and to determine the relative numbers of cells comprising various rearrangements within a patient's blood sample. Also, combining the second reaction mix with a portion of the first reaction mix allows for higher concentrations of target-specific primers to be added to the first reaction mix, resulting in greater sensitivity in the first amplification reaction. It is the combination of specificity and sensitivity, along with the ability to achieve quantitative results by use of a method such as the arm-PCR method that allows a sufficiently sensitive and quantitative assessment of the type and number of clonotypes in a population of cells to produce a Delta Index that is of diagnostic use.

Clonal expansion due to recognition of antigen results in a larger population of cells that recognize that particular antigen, and evaluating cells by their relative numbers provides a method for determining whether an antigen exposure has influenced expansion of antibody-producing B cells or receptor-bearing T cells. This is helpful for evaluating whether there may be a particular population of cells prevalent in individuals who have been diagnosed with a particular disease. For example, the method may be especially helpful in evaluating whether or not a treatment or vaccine has achieved the desired immune response in individuals to whom the treatment or vaccine has been given.

Primers for amplifying and sequencing variable regions of immune system cells are available commercially, and have been described in publication such as the inventor's published patent applications WO2009137255 and US201000021896A1, both of which are herein incorporated by reference in their entirety.

There are several commercially available high-throughput sequencing technologies, such as Hoffman-LaRoche, Inc.'s 454 sequencing system. In the 454° sequencing method, for example, the A and B adaptor are linked onto PCR products either during PCR or ligated on after the PCR reaction. The adaptors are used for amplification and sequencing steps. When done in conjunction with the arm-PCR technique, A and B adaptors may be used as common primers (which are sometimes referred to as "communal primers" or "superprimers") in the amplification reactions. After A and B adaptors have been physically attached to a sample library (such as PCR amplicons), a single-stranded DNA library is prepared using techniques known to those of skill in the art. The single-stranded DNA library is immobilized onto specifically-designed DNA capture beads. Each bead carries a unique singled-stranded DNA library fragment. The bead-bound library is emulsified with amplification reagents in a water-in-oil mixture, producing microreactors, each containing just one bead with one unique sample-library fragment. Each unique sample library fragment is amplified within its own microreactor, excluding competing or contaminating sequences. Amplification of the entire fragment collection is done in parallel. For each fragment, this results in copy numbers of several million per bead. Subsequently, the emulsion PCR is broken while the amplified fragments remain bound to their specific beads. The clonally amplified fragments are enriched and loaded onto a PicoTiterPlate® device for sequencing. The diameter of the PicoTiterPlate® wells allows for only one bead per well. After addition of sequencing enzymes, the fluidics subsystem of the sequencing instrument flows individual nucleotides in a fixed order across the hundreds of thousands of wells each containing a single bead. Addition of one (or more) nucleotide(s) complementary to the template strand results in a chemilluminescent signal recorded by a CCD camera within the instrument. The combination of signal intensity and positional information generated across the PicoTiterPlate® device allows the software to determine the sequence of more than 1,000,000 individual reads, each is up to about 450 base pairs, with the GS FLX system.

Figure 1:
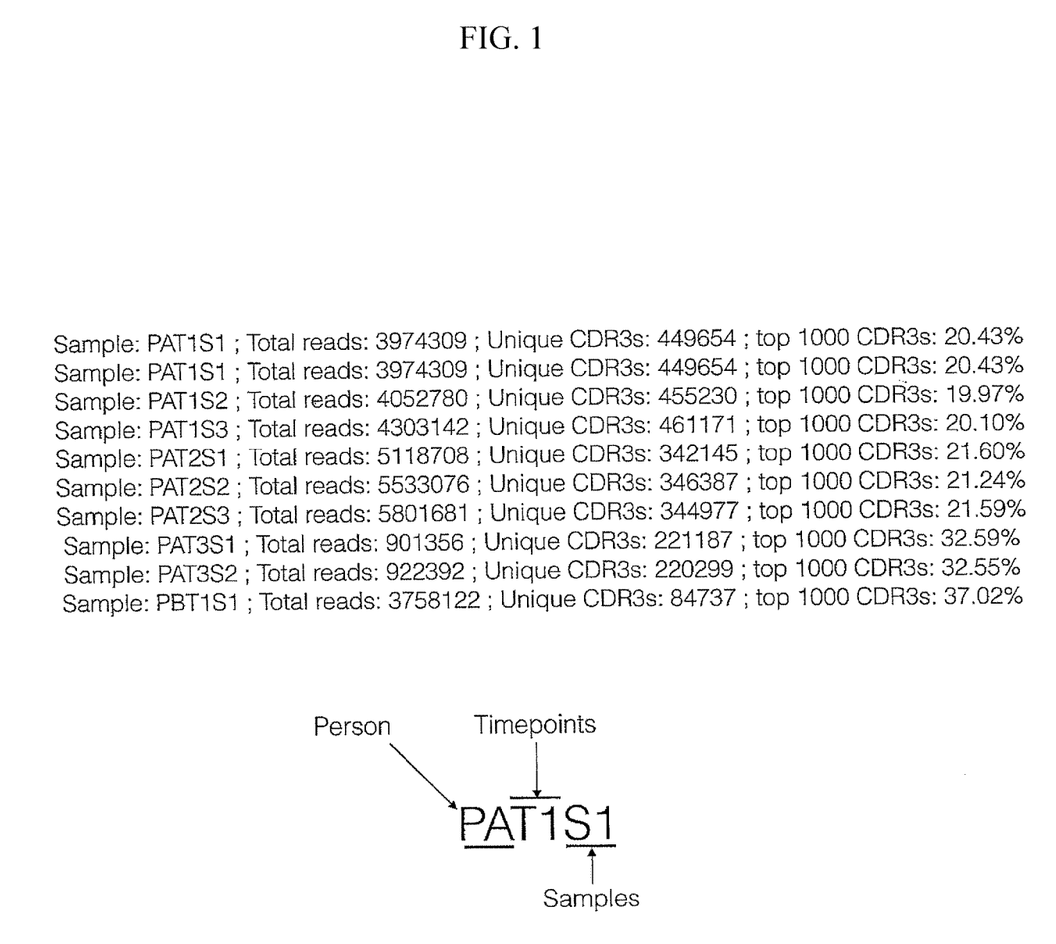
FIG. 1 is an illustration of raw CDR3 sequencing data obtained from patients at different time points.

In one embodiment of the invention, sequencing information from the CDR3 region of T cells, B cells, and/or subsets of T or B cells is obtained from a single patient. As illustrated in FIG. 1, these cells may be collected at varying time points. For example, multiple samples may be collected from the same patient at the same time point (PAT1S1, PAT1S2). In this embodiment, samples are collected before the commencement of a treatment regime. As will be described in more detail below, analysis of sequence information from samples taken at the same time point allows for the establishment of an initial or baseline immune repertoire turnover rate of the patient's most dynamic immune cells. In an additional embodiment, the methods of the invention are practiced on samples collected from the same patient at different time points (PAT1S1, PAT2S1) (FIG. 1). In one embodiment, samples may be collected before, during and after a treatment regime, the timing of which may be dictated by the patient's practitioner. Analysis of this sequence information allows one to determine a change in the immune repertoire turnover rate of the patient's most dynamic immune cells resulting from the treatment regime.

Differences in how the sample is collected, the number of cells collected, the number of sequencing reads obtained (i.e., the number of sequences obtained from a sample) and the number of CDR3 sequences sampled makes comparison of two samples impossible without first normalizing the samples to a common read count. A reference must therefore be established as a basis of comparison for later measurements. Therefore, having obtained the sequences using a quantitative and/or semi-quantitative method, it is then preferable to normalize the data to account for such differences.

Figure 3:
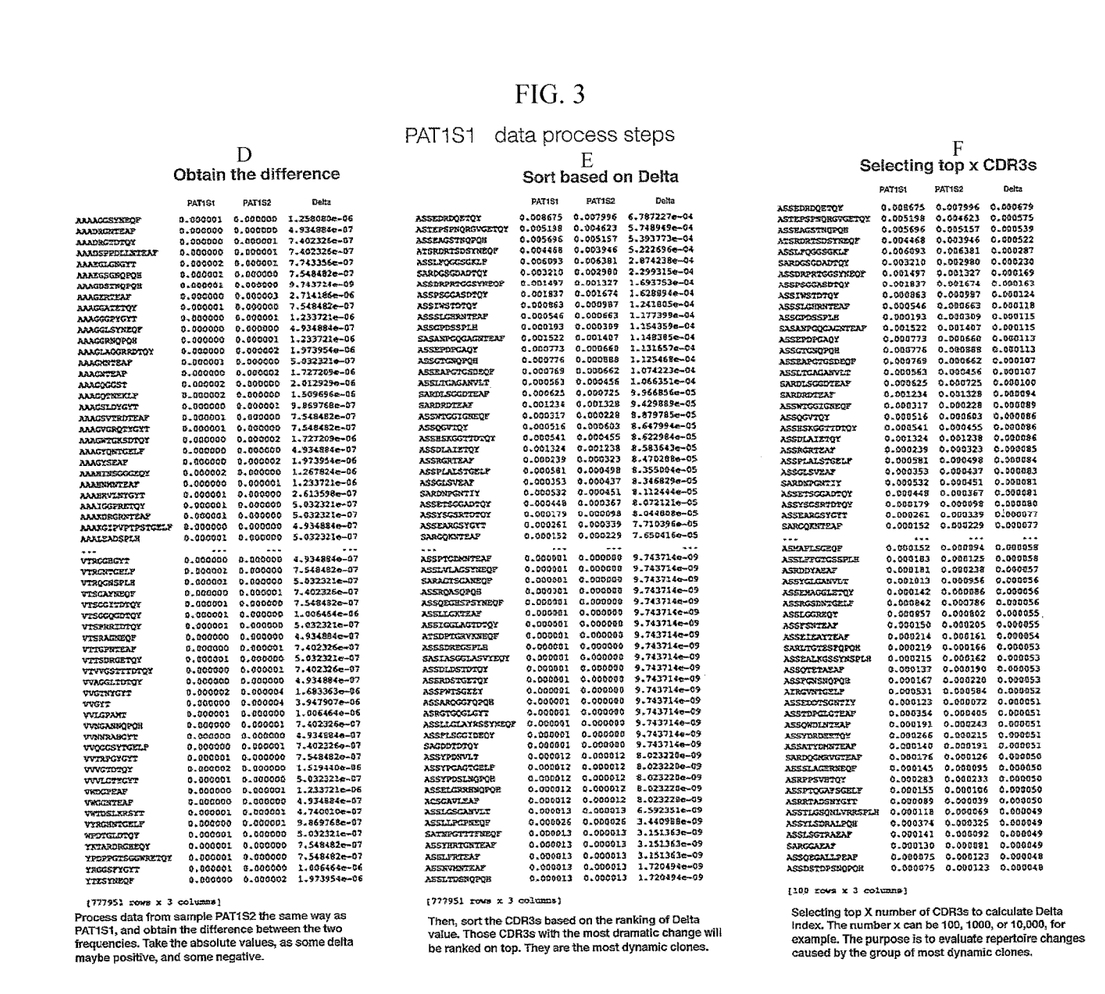
FIG. 3 represents the calculation utilized in determining the Delta Index of two samples collected from the same patient: Column D represents the absolute difference between the frequencies of each CDR3 read count in each sample; Column E represents the calculation of the impact range of the two samples; and Column F represents the calculation of the Delta Index for the two samples.

FIGS. 2 and 3 illustrate the process of calculation the baseline change in the immune repertoire. Column A of FIG. 2 represents raw sequence data for a number of CDR3 regions of a population of immune cells from a first patient sample. As is evident from column A, each detected gene sequence has an accompanying frequency of 10 million (reads). In one embodiment of the invention, each sample is normalized to 10 million reads to account for these discrepancies. In this embodiment, a normalized read count is obtained by multiplying the read count (i.e., the number of times each unique CDR3 sequence is detected in the sample) for each CDR3 sequence by a normalization factor (10 million/total number of reads for the sample) (column B), which is then divided by 10 million (column C). Although the present example normalizes the read count to 10 million, the count may be normalized to other cell concentrations in other embodiments.

To establish a baseline repertoire turnover rate for an individual, the normalized sequence data from two samples collected at a single time period (PAT1S1 and PAT1S2) are then compared. Referring now to FIG. 3, the absolute difference between the frequencies of each CDR3 read count in each sample is determined (column D). Because the present method is used to determine the change in an individual's immune repertoire, all quantitative changes (i.e., the increase or decrease in the frequency of a unique CDR3 sequence) are included in these calculations. In an additional embodiment, the absolute difference between the frequencies of each CDR3 sequence will also include qualitative changes. For example, the fact that a specific CDR3 sequence may be present in the first sample but absent from the second sample (or vice versa) will be in the calculations for determining the absolute difference in clonotype diversity between the two samples.

Referring again to FIG. 3, the next step in determining the baseline immune repertoire turnover rate for a patient includes the calculation of the impact range of the two samples (column E). As used herein, the impact range is calculated by determining the percentage of the patient's immune repertoire contributed by the most dynamic clones. It is necessary to determine the impact range so that sampling differences between the two populations may be eliminated. As described previously, such sampling inconsistencies may include, for example, differences in the number of cells included in the patient sample, differences in the amplification efficiency during arm-PCR, introduction of sequencing bias and differences in sequencing depth. The presence of these sample variables makes it impossible to compare the frequency variability between the two populations. Normalizing the sequencing data to 10 million reads, as described above, helps to eliminate some of these inconsistencies. However, further steps, such as calculating the impact range, must be taken to enable the analysis of the vast amount of sequencing data and to allow for the direct comparison of the two samples. The variables discussed above will mask any frequency changes and make such a comparison impossible. In one embodiment, the impact range is determined by calculating the percent of the patient's immune repertoire contributed by the 100 clones with the biggest frequency difference between samples. As illustrated in FIG. 4, other numbers of clones may be included in the calculation of the impact range in other embodiments, for example the 1,000 or 10,000 clones with the biggest frequency difference between the samples.

In the next step illustrated in FIG. 3, column F, the Delta Index is calculated for the two samples. As used herein, the Delta Index represents the total percentage of the sequenced CDR3 clones within the impact range that exhibit a frequency difference between the first and second samples. In the example illustrated in FIG. 4, column H, the impact range of samples 1 and 2 (averaged) is 7.27%, indicating that the 100 most dynamic CDR3 clones make up 7.27% of the sequenced immune repertoire of the patient. In the final step, the Delta Index is calculated for the two samples. In this embodiment, the Delta Index is the percentage of the CDR3 clones included in the impact range that has changed between sample 1 and sample 2. As illustrated in FIG. 4, column H, the Delta Index of 6.53% is a calculation of the baseline immune repertoire turnover for the patient, calculated from two samples collected at the same time point, for example, before the start of a health event.

After establishing the baseline immune repertoire turnover rate, the Delta Index then be calculated for two samples collected at different time periods. In one embodiment, a first sample may be collected before the start of treatment and a second sample collected during, or after the treatment is completed. As illustrated in FIG. 4, the raw CDR3 sequence data from two samples collected at different time points (PAT1S1 and PAT2S1) is: (1) normalized; (2) the absolute difference between the frequencies calculated; (3) the impact range of the two samples is calculated; and (4) the Delta Index determined for the two samples. These steps are performed in the same manner as described previously in regards to FIGS. 2-4 (i.e., the same manner as in calculating the baseline Delta Index). As further illustrated in FIG. 4, the signal to noise ratio of the Delta Index calculation may then be determined by comparing the baseline Delta Index to the experimental Delta Index, as illustrated by the following calculation: Signal/Noise=Delta Index (PAT1S1-PAT2S1)/Delta Index (PAT1S1-PAT1S2) In the embodiment illustrated in FIG. 4, the selection of an impact range of 100 produces the lowest signal to noise ratio and provides results with the less noise.

The present invention allows for the calculation of the repertoire rate of the most dynamic immune cells. The steps of the method involve the manipulation of vast amounts of sequence data, for example when normalizing sample sizes, obtaining frequency values for each CDR3, obtaining absolute frequency changes, and calculating impact ranges. These calculations are necessary to take into account that some clones may be upregulated during a health event, others may be downregulated, some clones may disappear at second time point, and some new clones may appear at the different time point. The present invention overcomes these problems by determining overall repertoire changes and quantifying the changes associated with each CDR3. The present methods allow for the analysis of a vast amount of sequencing data while eliminating sampling and sequencing inconsistencies that have previously made the comparison of immune repertoire changes impossible.

EXAMPLES

Example 1

Delta Index Calculations for Patient Samples

Two whole blood samples were collected from each of two healthy individuals at three month intervals. Two next generation sequencing (NGS) protocols were performed on the samples from each individual. RNA was extracted from, on average, 1 million cells, and arm-PCR was used to generate the NGS library. Sequencing was performed using the Illumina HiSeq® instrument.

FIG. 5 Illustrates the Calculated Delta Index for Several Sample Groups:

Group A represents a single sample taken from one patient, where the sample is split into two subsamples. The Delta Index is 0.00% for this population because the two samples were collected at the same time point with no sample variation.

Group B represents multiple samples taken from the same individual at the same time point. The repertoire change (Delta Index) is measured at between 3.88% and 6.53%. These types of sample are useful for calculating the baseline repertoire change for an individual.

Group C represents samples taken from the same individual at two different time points with an interval of one or two days. These calculated repertoire changes may vary from between 0% and 100% and are useful in determining repertoire changes caused by a health event.

Group D represents samples taken from the same individual at two different time points with an interval of three months. These calculated repertoire changes may vary from between 0% and 100% and are useful in determining repertoire changes caused by a health event.

Group E represents samples taken from different individuals at different time points. In this situation the Delta Index is expected to be near 100%.

Example 2

Healthy Patient Samples

Two whole blood samples were collected from each of 19 healthy individuals at three month intervals. Two NGS protocols were performed on the samples from each individual. RNA was extracted from, on average, 1 million cells, and arm-PCR was used to generate the NGS library. Sequencing was performed using the Illumina HiSeq® instrument. On average, 5 million T cell receptor molecules were sequenced for each sample (10 million total reads per individual). Approximately 100,000 to 300,000 unique CDR3 sequences were obtained from each sample.

Table 1 illustrates the results of analyzing close to 200 million sequence reads (one read=one molecule), including the calculated Delta Index, with a range of 5.52% to 23.33%, with an average of 13%.

TABLE 1

Calculated Delta Index

| Normal Samples | Delta Index (%) |
|---|---|
| 1 | 14.95 |
| 2 | 7.29 |
| 3 | 23.33 |
| 4 | 11.05 |
| 5 | 22.77 |
| 6 | 8.53 |
| 7 | 10.91 |
| 8 | 6.5 |
| 9 | 14.37 |
| 10 | 9.93 |
| 11 | 20.64 |
| 12 | 20.26 |
| 13 | 6.23 |
| 14 | 10.26 |
| 15 | 6.23 |
| 16 | 21.16 |
| 17 | 5.52 |
| 18 | 13.62 |
| 19 | 14.25 |

Example 3

Breast Cancer Samples

Samples were obtained from 12 breast cancer patients undergoing neoadjuvant treatment, i.e., chemotherapy before surgery to reduce the tumor burden before surgery.

Peripheral blood samples were collected pre- and post-treatment. Two NGS protocols were performed on the samples from each individual. RNA was extracted from, on average, 1 million cells, and arm-PCR was used to generate the NGS library. Sequencing was performed using the Illumina HiSeq® instrument. As illustrated in Table 2, the calculated Delta Index range was from 20.49% to 97%, with an average 58.85%.

TABLE 2

Calculated Delta Index

| Patient # | Delta Index (%) |
|---|---|
| 1 | 21.72 |
| 2 | 20.49 |
| 3 | 83.39 |
| 4 | 64.21 |
| 5 | 75.62 |
| 6 | 66.30 |
| 7 | 59.19 |
| 8 | 97.86 |
| 9 | 72.57 |
| 10 | 61.77 |
| 11 | 48.06 |
| 12 | 35.12 |

These calculated Delta Index ranges indicate a significantly higher repertoire turnover rate as compared to that observed for healthy individuals (Table 1). Calculating the immune repertoire turnover rate, using the methodologies described herein, offers several advantages compared with current methods. The methodologies disclosed herein may, for example, help to evaluate treatment outcomes or to indicate the onset of a disease state.

The methodologies and the various embodiments thereof described herein are exemplary. Various other embodiments of the methodologies described herein are possible.

Now, therefore, the following is claimed:

1. A method of calculating the change in the immune repertoire of a subject, comprising the steps of:
   quantifying clonotypes of immune cells in a population or subpopulation of immune cells in a first sample and a second sample collected from the same patient using arm-PCR and next generation sequencing;
   calculating frequency data for the first sample and the second sample by identifying the frequency of each clonotype;
   normalizing the frequency data for the first sample and the second sample;
   determining the absolute difference in the frequency of each clonotype present in the first sample and the second sample; and
   determining the clonotypes common to the first sample and the second sample with the largest frequency change.

2. The method of claim 1, wherein the clonotypes are CDR3 clonotypes.

3. The method of claim 1, wherein the first sample and the second sample are collected at the same time point.

4. The method of claim 1, wherein the first sample and the second sample are collected at different time points.

5. The method of claim 1, wherein at least 100 clonotypes with the greatest frequency change are identified.

6. The method of claim 1, wherein each sample comprises white blood cells.

7. The method of claim 1, wherein the subject is healthy.

8. The method of claim 1, wherein the subject has been diagnosed with, or is suspected of having, a disease.

9. The method of claim 1, wherein the subject is treated with an immune therapy.

10. The method of claim 9, wherein the subject receives immune therapy after the first sample is collected.

11. A method of calculating the change in the immune repertoire of a subject, comprising the steps of:

collecting at least two sample populations of white blood cells from a subject;

separately amplifying polynucleotides from each population of white blood cells in a reaction mix comprising target-specific nested primers to produce a set of first amplicons, at least a portion of the target-specific nested primers comprising additional nucleotides which, during amplification, serve as a template for incorporating into the first amplicons a binding site for at least one common primer;

separately transferring a portion of each of the first reaction mixes containing the first amplicons to second reaction mixes comprising at least one common primer;

for each population, amplifying, using the at least one common primer, the first amplicons to produce a set of second amplicons;

sequencing each of the second amplicons to identify the frequency of specific CDR3 regions present in the sample;

normalizing the CDR3 frequency data;

comparing the normalized CDR3 frequency data of the first sample and the second sample to determine the absolute difference between the frequency of each CDR3 sequence; and determining the CDR3 sequences, common to the first sample and the second sample, with the largest frequency changes.

12. The method of claim 11, wherein the first sample and the second sample are collected at the same time point.

13. The method of claim 11, wherein the first sample and the second sample are collected at different time points.

14. The method of claim 11, wherein the subject is healthy.

15. The method of claim 11, wherein the subject has been diagnosed with, or is suspected of having, a disease.

16. The method of claim 11, wherein the subject is treated with an immune therapy.

17. The method of claim 16, wherein the subject receives immune therapy after the first sample is collected.

* * * * *